United States Patent [19]

Gray

[11] Patent Number: 5,059,195

[45] Date of Patent: Oct. 22, 1991

[54] SURGICAL INSTRUMENT WITH DETACHABLE TOOL MEMBER

[76] Inventor: Frank B. Gray, 5104 Lyons View Dr., Knoxville, Tenn. 37919

[21] Appl. No.: 478,931

[22] Filed: Feb. 12, 1990

Related U.S. Application Data

[63] Continuation-in-part of Ser. No. 226,888, Aug. 1, 1988, abandoned, which is a continuation-in-part of Ser. No. 55,029, May 28, 1987, Pat. No. 4,813,413.

[51] Int. Cl.$^5$ ............................................. A61B 17/00
[52] U.S. Cl. ........................................ 606/84; 81/423; 408/239 R
[58] Field of Search .................. 606/79, 84, 85, 167; 81/423, 421; 30/337; 269/259, 261, 262; 409/233; 279/102, 8, 89–91; 408/239 R; 16/DIG. 24

[56] References Cited

U.S. PATENT DOCUMENTS

| | | | |
|---|---|---|---|
| 280,599 | 7/1883 | Gardner | 30/337 |
| 1,064,101 | 6/1913 | Smith | 30/337 |
| 2,562,419 | 7/1951 | Ferris | 606/72 X |
| 4,035,100 | 7/1977 | Kruger et al. | 279/102 |
| 4,124,026 | 11/1978 | Berner et al. | 606/85 X |
| 4,314,565 | 2/1982 | Lee | 128/753 |

FOREIGN PATENT DOCUMENTS 144607 10/1920 United Kingdom .................. 30/337

*Primary Examiner*—Michael H. Thaler

*Attorney, Agent, or Firm*—Pitts & Brittian

[57] ABSTRACT

An improved manual instrument for use in performing surgical procedures with the tool portion of the instrument being readily detachable from the handle portion. This instrument has a coupling between the handle portion and the tool portion that permits a full transfer of all forces, including axial, transverse and rotational, from the handle portion to the tool portion during use of the instrument. The primary portions of the coupling are mating (complementary) conical nondeformable surfaces on one end of the tool member and one end of the handle member. In the preferred form, the two mating surfaces are also provided with flat portions that prevent relative rotation of the components. Further, these mating flat portions permit a selected orientation between external portions of the handle member and the work portion of the tools member. The structure described permits the rapid exchange of tool members with respect to a given handle member when, for example, the work portion of the tool member becomes damaged or when a tool member with a work portion of a different configuration is required during the surgical procedure. A transfixing rod that passes axially through the handle member is treadably engaged with the tool member when the parts are to be joined. In the preferred embodiment, this rod has a knurled knob at an opposite end to permit rapid rotation of the rod by a user of the instrument. Several embodiments of mating surfaces of the coupling are described.

18 Claims, 3 Drawing Sheets

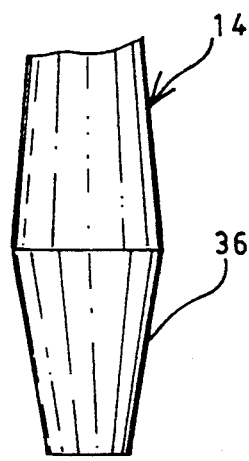 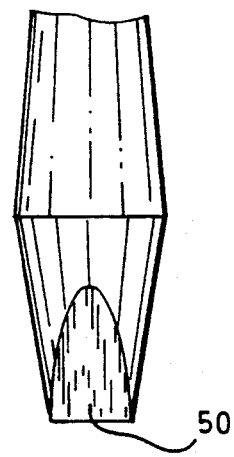 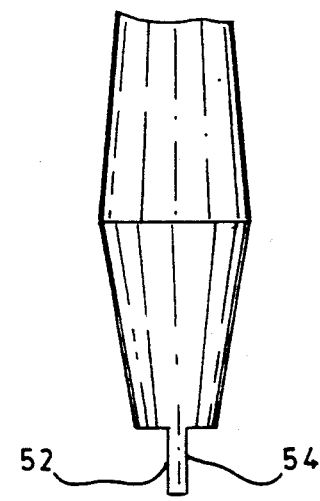
FIG. 4A    FIG. 4B    FIG. 4C
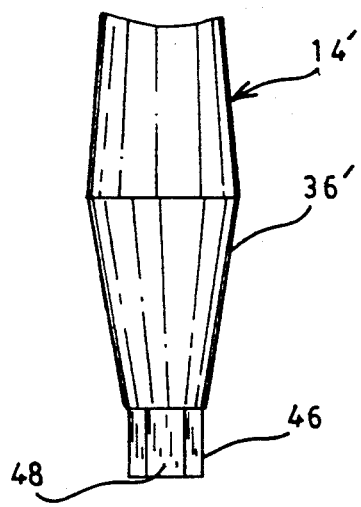 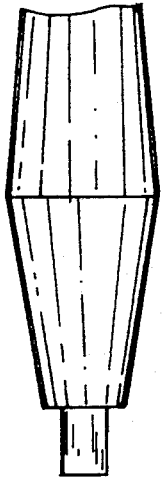 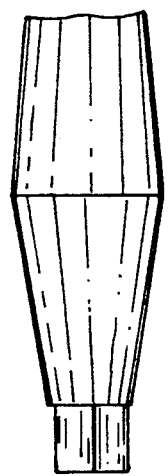
FIG. 4D    FIG. 4E    FIG. 4F

SURGICAL INSTRUMENT WITH DETACHABLE TOOL MEMBER

DESCRIPTION

This is a continuation-in-part application of parent application Ser. No. 226,888 filed Aug. 1, 1988, now abandoned, which was a continuation-in-part of application Ser. No. 55,029 filed May 28, 1987, now U.S. Pat. No. 4,813,413 which issued on Mar. 21, 1989.

TECHNICAL FIELD

This invention relates to manually operated surgical instruments, and more particularly to an improved manual surgical instrument having a readily detachable tool member which provides for complete transmission of transverse and axial forces from the handle member to the tool member.

BACKGROUND ART

In the general art of manual instruments for performing orthopedic surgery, such as osteotomies, curets, gouges, chisels, and the like, the instruments have been fabricated of a single piece to form both a handle and the tool portion for performing the surgical operations. Each instrument was configured such that the tool portion was associated with the particular form of operation. Because these instruments have been integrally formed, when the tool portion becomes worn or broken through use, the entire instrument must be either reconditioned or discarded. If the damage occurs during an operation, a new instrument must be readily available to the surgeon so as to continue the operation. Of course, replacement and/or reconditioning of such instruments can be extremely costly.

Certain tools outside of the medical field, such as wrenches, have been devised which have tool portions which are detachable from the tool handle so as to permit the replacement of the tool portion when desired. Further, some of these tools are designed to permit interchangeable tool portions for tools are disclosed in U.S. Pat. No: 1,006,661, issued to M. A. Knapp on Oct. 24, 1911; 1,413,101, issued to S. J. Cushing on Apr. 18, 1922; 2,231,252, issued to W. L. Chesterman on Feb. 11, 1941; 2,832,246, issued to F. W. Livermont on Apr. 29, 1958; 2,832,943, issued to M. Cutler on Apr. 29, 1958; and 3,039,340, issued to F. W. Livermont on June 19, 1962.

The coupling means utilized by the devices of these patents, as used to releasably secure the tool portions to the handle portions, are not readily adaptable to use with surgical instruments. In this regard, most surgical instruments are relatively small in size, and the coupling means must be capable of being scaled accordingly while producing a strong and durable coupling. It is necessary, in the case of surgical instruments, that various forces be delivered to the handle portions, with these forces being fully delivered to the tool portions. This includes axial forces, as produced by a "hammer", and transverse forces created by movement of the handle portion by the surgeon. Further, the coupling mechanism that would be used with surgical instruments must permit very rapid changing of the tool portion: the couplings described in the above-cited patents will not meet these requirements.

Other tools and devices generally of interest are disclosed in the following U.S. Pat. No: 4,473,070, issued to L. S. Matthews, et al. on Sept. 25, 1984; 4,601,289, issued to S. J. Chiarizzio, et al on July 22, 1986; 3,685,058, issued to R. G. Tronzo on Aug. 22, 1972; 2,312,B69, issued to C. A. Boyer on Mar. 2, 1943; Des. 272,648, issued to R. C. Bolesky, et al. on Feb. 14, 1984; 4,587,964, issued to C. B. Walker on May 13, 1986; and 4,124,026, issued to K. Berner, et al. on Nov. 7, 1978. See also German Pat. No. 2,906,068, issued on June 25, 1980 and the SYNTHES Product Catalog.

A departure from the one-piece surgical instrument was made with the instrument shown and described in the above-referenced U.S. Pat. No. 4,813,413 issued to the present inventor on Mar. 21, 1989. The teachings of this patent are incorporated herein by reference. The instrument of this patent provided for the rapid exchange of the tool portion for whatever reason: damage to the tool member; or the requirement for a tool member of a different configuration. This permitted a surgeon to retain a grip on the handle during this exchange such that there was little lost motion caused by the change. While most of the desired characteristics of a surgical instrument were present with the device of this patent, some movement (principally transverse) between the tool member and the handle member occurs even when very close tolerances are used in the making of the coupling components.

Therefore, it is an object of the present invention to provide a surgical instrument that has a readily detachable tool member.

A further object of the present invention is to provide a surgical instrument having a coupling member between a handle member and a detachable tool member that permits complete transfer of all transverse and axial forces from the handle member to the tool member.

It is also an object of the present invention to provide a surgical instrument having a readily detachable tool member that, in addition to transmitting all transverse and axial forces from the handle member to the tool member, further prevents rotational movement between the tool member and the handle.

Still another object of the present invention is to provide a surgical instrument having a readily detachable tool member that, in addition to transmitting all transverse and axial forces from the handle member to the tool member, further automatically orients the tool member to a desirable orientation with respect to the handle member.

These and other objects of the present invention will become apparent upon a consideration of the drawings that follow, together with the detailed description given thereafter.

DISCLOSURE OF THE INVENTION

In accordance with the present invention, there is provided a surgical instrument that has a handle member and a readily detachable tool member. In order to achieve a full transmission of forces applied to the handle into the tool member, the handle member of the preferred embodiment has a generally conical receptor at one end into which a generally conical end of the tool member is fitted. The contours of the two portions to be joined are complementary such that intimate contact is achieved. In order that the conical end portion of the tool member is fully drawn into the receptor of the handle member, a rod passes through an axial passageway in the handle member and is threadably received in a threaded receptor in the tool member. By rotating the rod in a first direction, close coupling of the components is achieved; rotation in the opposite direction disconnects the components. In the preferred embodiment, a knob is provided on the handle end of the rod for ready rotation of the rod by a user of the instrument. Further, in the preferred embodiment, the mating surfaces of the handle member and the tool member are provided with complementary flat areas to prevent rotation of the tool member with respect to the handle member. By proper placement of the flat areas, a desired rotational orientation can be achieved between the tool member and the exterior surface of the handle member.

BRIEF DESCRIPTION OF THE DRAWINGS

FIG. 4A is a fragmental drawing showing the contour of the connector end of the tool member of FIG. 2.

FIG. 4B is a fragmental drawing showing a contour of the connector end of another embodiment of tool member.

FIG. 4C is a fragmental drawing showing a contour of the connector end of still another embodiment of tool member useful for the present invention.

FIG. 4D is a fragmental drawing showing the contour of the connector end of the tool member of FIG. 3.

FIG. 4E is a fragmental drawing showing a further embodiment of a connector end of a tool member as useful for the present invention.

FIG. 4F is a fragmental drawing showing another embodiment of a connector end of a tool member useful for the present invention.

BEST MODE FOR CARRYING OUT THE INVENTION

Figure 1:
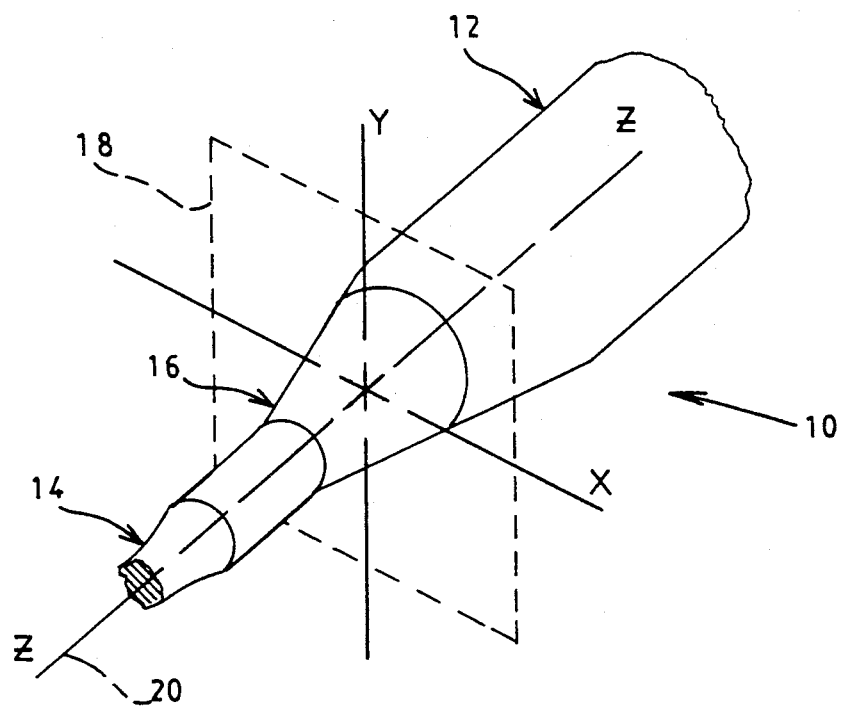
FIG. 1 is a diagrammatic drawing of a surgical instrument according to the present invention in which directions are established in order to describe orientation of the tool member with respect to the handle member of the embodiments depicted in subsequent drawings.

In order to fully understand the requirements of an improved surgical instrument, FIG. 1 presents the relative directions of motion that must be provided for with this instrument indicated generally at 10. As specified, the instrument 10 has a handle member 12 and a readily detachable tool member 14. They are releasably joined at a coupling point indicated at 16. Details of these components will be given hereinafter. In this FIG. 1, transverse movement (or forces to produce transverse movement) are those that occur essentially in the X-Y plane illustrated at 18. This plane is perpendicular to the axial direction, indicated as the Z-coordinate, with that axis identified by the numeral 20. Thus, if force is applied axially to the handle member 12, this force must be transmitted along the axis 20 to the tool member 14 without any loss. Similarly, any transverse force applied to the handle member 12 must be transmitted to the tool member 14 without any loss. It will be seen from the following discussion how this transfer of forces without loss is accomplished with the present invention.

Figure 2:
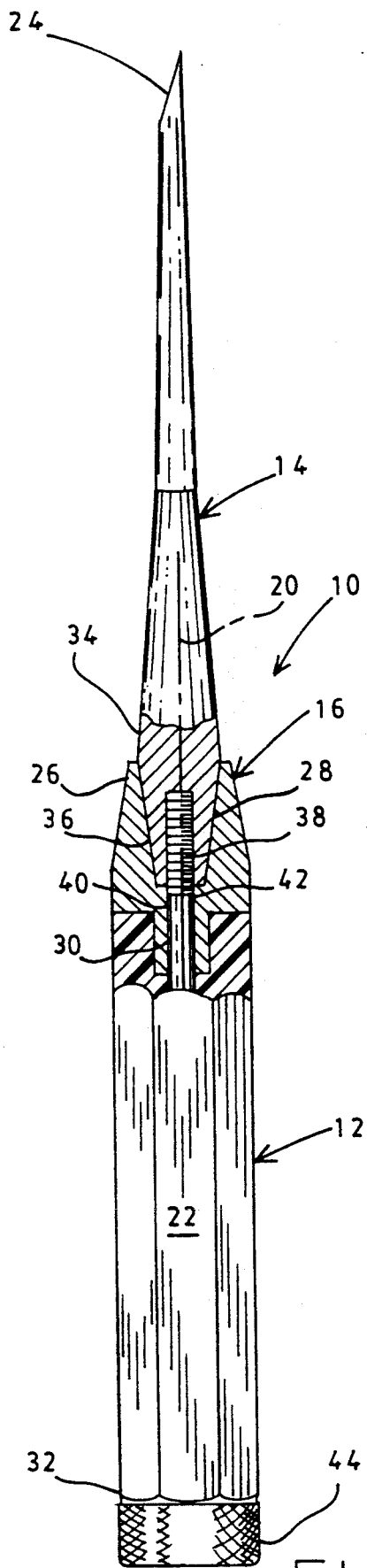
FIG. 2 is a drawing, partially cut away, showing one embodiment according to the present invention.

Referring now to FIG. 2, shown therein is one embodiment of the present invention. In this particular embodiment 10, the handle member is illustrated as having a generally hexagonal exterior surface 22, and being primarily fabricated from a suitable plastic. However, the exterior configuration can be of any design to properly fit the hand of a user, and the handle member can be fabricated of any suitable material, including a metal. The particular tool member 14 of this embodiment is illustrated as having a chisel-shaped distal end 24; however, the distal end can be shaped for the particular surgical procedure to be performed by the user of the instrument.

The handle 12 has a first end 26 which, with the remainder of the handle being a plastic, preferably is fabricated from a metal or other non-deformable material. This first end is provided with a receptor 28 which, in this embodiment, defines a conical interior surface that converges in a direction away from the first end. This conical surface is symmetrical around the axis 20 and is preferably a "unitary surface", i.e., is a continuous conical surface. The handle 12 further is provided with an axial passageway 30, as shown, that extends from the receptor 28 to the second end 32 of the handle member 12.

In order that the tool member 14 can be rigidly connected to the handle member, a first end 34 of the tool member is provided with a external surface 36 (preferably unitary) that is complementary to the interior surface of the receptor 28 of the handle member 12. This surface 36 must present a non-deformable surface such that no relative movement occurs between the handle member 12 and the tool member 14 when this first end 34 of the tool member is inserted in the receptor 28. Typically the entire tool member 14 is fabricated from a suitable metal so that this surface 36 presents a metal surface. In the preferred embodiment, the exterior surface 36 of the tool member 14 is formed from the same material of the receptor 28 of the handle member 12; e.g., both are the same metal. The first end 34 of the tool member is provided with a threaded receptor 38 oriented along the axis 20.

A third element of the present invention is a rod 40 that passes through the passageway 30 in the handle member 12. This rod, referred to as a "transfixing rod" in view of its role in the present instrument, has a threaded first end 42 for threadable engagement with the threaded receptor 38. A further or second end 44 of the rod 40 is formed, in this embodiment, as a knurled knob proximate the second end 32 of the handle member 12. This knob facilitates the rapid rotation of the transfixing rod 40 in either direction: in a first direction to advance the threaded end 42 into the receptor 38; and in an opposite direction to remove this threaded end from the receptor. When the threaded end 42 advances within the threaded receptor 38, the exterior surface 36 of the first end 34 of the tool member 14 is drawn into the receptor 28 until intimate contact is made between this external surface and the internal surface of the receptor. When this intimate contact is made, any force (either transverse or axial) applied to the handle 12 is fully transmitted to the tool member 14 without any relative movement between the components in accordance with one of the objects of the present invention. Thus, if an axial blow is applied to the handle member at the end 32 (as against the knob 44), the full force is transmitted to the distal end 24 of the tool member. Movement of the handle member 12 in any other direction is likewise fully transmitted to the tool member 14.

Figure 3:
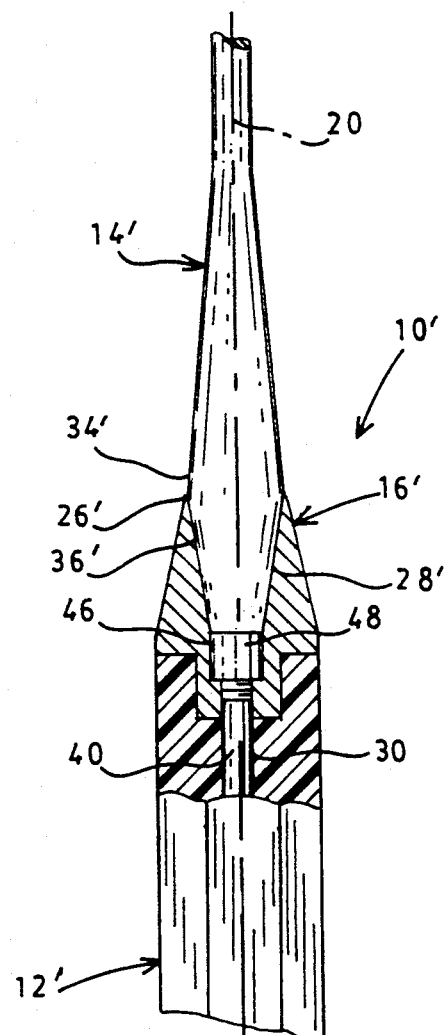
FIG. 3 is a drawing, partially cut away, showing another embodiment according to the present invention.

Another embodiment of an instrument according to the present invention is shown generally at 10' in FIG. 3. It will be understood that this embodiment can have external features similar to those shown in FIG. 2; therefore, the extreme end 32 of the handle 12', the rod operating knob 44, and the distal end 24 of the tool member 14' are not 25 shown in this figure. This embodiment 10' differs from that of FIG. 2 with regard to the configuration of the coupling means 16'. The tool member, at the first end has an external surface that includes a conical portion 36' of the same general configuration as the previous embodiment; however, in addition it has an axial extension 46 that defines a hexagonal cross-section producing a plurality of flat areas 48 that are substantially parallel to the axis 20. In a like manner, the handle member 12' has a first end 26' that is provided with a receptor 28' that has an interior surface that is again complementary to that of the exterior surface of the first end of the tool member.

Accordingly, this interior surface of the receptor 28' has a conical portion to mate with the conical portion of the tool member as well as an extension of the receptor 28' that mates with the surfaces of the hexagonal extension 46 of the tool member. As with the previously-described embodiment, there is a transfixing rod 40 that is threadably engageable with a threaded receptor (not shown) in the first end of the tool member to provide the means for producing an intimate contact between the respective conical surface portions of the first end 34' of the tool member 14' and the receptor 28' of the tool member 12'.

The construction of the embodiment of FIG. 3 provides the same firm locking of the tool member and the handle member, as provided with the embodiment of FIG. 2. In addition, this embodiment 10' provides two other features for a surgical tool. One feature is that the locking hexagonal surfaces of the coupling means 16' absolutely eliminate any rotation between the handle member 12' and the tool member 14'. For some types of surgical procedures this absolute absence of relative rotation is essential. Another feature of the embodiment 10' is that the orientation of the distal end of the tool member 14'(the end that performs the surgical procedure) and the handle 12' can be assured. Thus, a user can retain a grip on the handle member 12' while the tool member 14' is replaced and can be assured that the distal end of the new tool member will have the same orientation as the previous tool member. This is an important feature to reduce time during the surgical procedure.

While the hexagonal configuration illustrated in FIG. 3 provides these antirotational and orientation features, other configurations of the tool member and the handle member receptor will also produce the same features and may be preferred for certain surgical instruments. Several typical embodiments of these configurations are illustrated in FIGS. 4A through 4F. For comparison purposes, FIG. 4A illustrates the configuration for the tool member coupling portion of the type shown in FIG. 2: the exterior surface being a truncated cone. FIG. 4B, showing another embodiment, utilizes one flat surface 50 contained within the conical surface that will prevent rotation and, if desired, provide proper orientation between the tool member and the handle member of an instrument of the present invention.

A further embodiment is illustrated in FIG. 4C wherein the conical portion of the tool member is provided with an extension in the general form of a blade. This provides a pair of opposite flat surfaces 52, 54 that are substantially parallel to the axis of the tool member with these flat surfaces preventing rotation and providing for alignment. The embodiment of FIG. 4D is like that shown in FIG. 3 wherein the extension 46 from the conical portion 36' has a hexagonal cross-section, with the flat surfaces 48 being substantially parallel to the axis. While these surfaces are shown as having this parallel relationship, it will be understood that the flat surfaces can taper inwardly toward the extreme end of the tool member (as in FIG. 4B) and still provide the antirotation feature and the alignment feature.

FIGS. 4E and 4F are other variations of the configuration for an extension from the conical portion. In FIG. 4E, the cross-section is square (or rectangular), and in FIG. 4F the cross-section is triangular.

Figure 5:
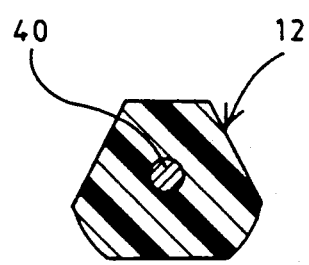
FIG. 5 is a cross-sectional drawing of a handle member of the present invention that is asymmetrical in configuration.

As stated above, the handle member 12 (or 12') can have any selected cross-sectional configuration. In FIGS. 2 and 3 this cross-sectional configuration is illustrated as being hexagonal. Another typical cross-sectional configuration is shown in FIG. 5, with the configuration being asymmetrical. It has been found by users that there is a preferred configuration for a given tool member; also, some users have a desired preference for any use. This is a feature of the present invention such that handle members and tool members can be matched as desired.

It will be understood from the previous discussion that the receptor in the end of the handle member will have a internal surface contour that substantially matches (is complementary) that of the tool member external surface. By "substantially" is meant that the conical portions provide intimate contact when the two parts are joined, and that there is at least one flat portion in the internal surface (for FIGS. 4B through 4F) to mate with any flat portion on the external surface of the tool member shaft.

From the foregoing, it will be understood that an improved surgical instrument has been shown and described that provides numerous functions not available with instruments of the prior art. Primary function is that of providing for the complete transfer of all forces from a handle member to a tool member, while providing for the exchange of tool members. This exchange may be necessary for one or more of several reasons: the tool being used has become damaged in some manner; a tool with a different shape is desired by the user; and a handle configuration can be chosen by the user to optimize grasp during a surgical procedure. Furthermore, certain embodiments of the present invention provide to prevention of rotation of the tool member with respect to the handle member. The structural items for prevention of the rotation also provide for a desired orientation of the tool member with respect to the handle member.

Although certain configurations of the components are illustrated for providing examples of the present invention, these are not given as an indication of any limitation of the present invention. It will be understood, for example, that the male and female portions of the coupling between the tool member and the handle member can be interchanged such that the external surface is a portion of the handle member, and the internal surface is a portion of the tool member. Therefore, the invention is to be limited only by the appended claims and their equivalents when read in conjunction with the detailed description of the invention.

I claim:

1. A manual surgical instrument for performing a selected surgical operation by a user, which comprises:

a tool member having a longitudinal axis, a first end portion configured to perform said selected surgical operation, and a second end configured to form a non-deformable first portion of a male/female connecting means of a selected configuration, said selected configuration including a conical portion symmetrical around said axis of said tool member, said second end portion provided with a threaded receptor aligned on said axis of said tool member;

a elongated handle member for grasp by a hand of said user, said handle member having a longitudinal axis, a first end portion and a second end portion, said handle member provided with a passageway extending along said longitudinal axis from said first end portion to said second end portion, said first end portion defining a non-deformable second portion of said male/female connecting means configured to be complementary to said first portion of said male/female connecting means said first end portion of said handle member including a conical portion, whereby when said first and second portions of said male/female connecting means are joined, said axis of said tool member and said axis of said handle member are coextensive;

said conical portions of said first and second portions of said connecting menas each having a complementary mating flat surface on a side surface thereof to thereby prevent rotation of, and provide selected rotational orientation between, said tool member and said handle member; and a transfixing rod for being received through said passageway in said handle member, said transfixing rod having a threaded first end for being threadably received in said threaded receptor of said tool member, and a second end extending from said second end portion of said handle member, said second end of said transfixing rod provided with means proximate said second end portion of said handle member for permitting said user to readily rotate said transfixing rod in a first direction to advance said threaded end into said threaded receptor of said tool member to produce intimate contact between said first and second non-deformable portions of said male/female connecting means, and for rotating said transfixing rod in a second direction to disengage said tool member from said handle member.

2. The surgical instrument of claim 1 wherein said first portion of said male/female connecting means is a male member at said second end of said tool member having an external surface including a conical portion converging toward said second end portion of said tool member, wherein said second portion of said male/female connecting means is a female portion at said first end portion of said handle member having a conical portion complementary to said conical portion of said external surface of said male portion.

3. A manual surgical instrument for performing a selected surgical operation by a user, which comprises:
a tool member having a longitudinal axis, a first end portion configured to perform said selected surgical operation, and a second end portion, said second end portion of said tool member defining an external non-deformable surface of a selected configuration, said external surface including a conical portion symmetrical around said axis of said tool member and converging toward said second end portion, said second end portion provided with a threaded receptor aligned on said axis of said tool member;

an elongated handle member for grasp by a hand of said user, said handle member having a longitudinal axis, a first end portion and a second end portion, said handle member provided with a passageway extending along said longitudinal axis from said first end portion to said second end portion, said first end portion being provided with a receptor communicating with said passageway, said receptor defining an interior non-deformable surface, including a conical portion, configured to be complementary to said external surface of said second end portion of said tool member so as to releasably receive said second end portion of said tool member with said axis of said tool member and said axis of said hand member being coextensive;

wherein said external surface of said second end portion of said tool member and said internal surface of said receptor of said first end of said handle member each include at least one complementary flat surface oriented with respect to said coextensive axes so as to prevent rotation of, and provide selected rotational orientation betwee, said tool member and said handle member; and a transfixing rod for being received through said passageway in said handle member, said transfixing rod having a threaded first end for being threadably received in said threaded receptor of said tool member, and a second end extending from said second end portion of said handle member, said second end of said transfixing rod provided with means proximate said second end of said handle member for permitting said user to readily rotate said transfixing rod in a first direction to advance said threaded end into said threaded receptor of said tool member to produce intimate contact between said external surface of said second end portion of said tool member and said internal surface of said receptor of said handle member, and for rotating said transfixing rod in a second direction to disengage said tool member from said handle member.

4. The surgical instrument of claim 3 wherein said at least one flat surface of said external surface of said tool member and said at least one flat surface of said internal surface of said receptor of said handle member is a flat surface on said conical portions oriented obliquely to said axis of said tool member and said axis of said handle member.

5. The surgical instrument of claim 3 wherein said second end portion of said tool member is provided with an axial extension and said at least one flat portion is provided on said extension, and said interior surface of said receptor of said handle member has a complementary portion to said extension and said at least one flat surface.

6. The surgical instrument of claim 3 wherein said means for permitting rotation of said transfixing rod is a knurled knob position contiguous to said second end portion of said handle member.

7. A manual surgical instrument for performing a selected surgical operation by a user, which comprises:
a tool member having a longitudinal axis, a first end portion configured to perform said selected surgical operation, and a second end portion, said second end portion of said tool member defining an external non-deformable surface of a selected configuration, said external surface including at least a conical portion symmetrical around said axis of said tool member and converging toward said second end portion and an axial extension extending from said conical portion, said axial extension having at least one flat surface oriented substantially parallel with said axis of said tool member, said second end portion provided with a threaded receptor aligned on said axis of said tool member;

an elongated handle member for grasp by a hand of said user, said handle member having a longitudinal axis, a first end portion and a second end portion, said handle member provided with a passageway extending along said longitudinal axis from said first end portion to said second end portion, said first end portion being provided with a receptor communicating with said passageway, said receptor defining an interior non-deformable surface configured to be complementary to said external surface of said second end portion of said tool member so as to releasably receive said second end portion of said tool member with said axis of said tool member and said axis of said handle member being coextensive; and a transfixing rod for being received through said passageway in said handle member, said transfixing rod having a threaded first end for being threadably received in said threaded receptor of said tool member, and a second end extending from said second end portion of said handle member, said second end of said transfixing rod provided with means proximate said second end of said handle member for readily permitting said user to rotate said transfixing rod in a first direction to advance said threaded end into said threaded receptor of said tool member to produce intimate frictional contact between said external surface of said second end portion of said tool member and said internal surface of said receptor of said handle member so as to prevent relative transverse, axial and rotational movement between said tool member and said handle during application of transverse, axial and rotational forces applied to said handle member, and for rotating said transfixing rod in a second direction to disengage said tool member from said handle member.

8. The surgical instrument of claim 7 wherein said non-deformable exterior surface of said second end portion of said tool member and said complementary non-deformable surface of said receptor at said first end portion of said handle member are formed of the same material.

9. The surgical instrument of claim 7 wherein said axial extension is provided with a plurality of flat portions substantially parallel to said axis of said tool member, and said receptor of said handle member is provided with complementary flat surface portions to closely receive said flat portions of said axial extension of said tool member.

10. The surgical instrument of claim 9 wherein said axial extension defines a hexagonal cross-section transverse to said axis of said tool member.

11. The surgical instrument of claim 9 wherein said axial extension defines a rectangular cross-section transverse to said axis of said tool member.

12. The surgical instrument of claim 7 wherein said means for permitting rotation of said transfixing rod is a knurled knob positioned contiguous to said second end portion of said handle member.

13. A manual surgical instrument for performing a selected surgical operation by a user, which comprises:
a tool member having a longitudinal axis, a first end portion configured to perform said selected surgical operation, and a second end portion, said second end portion of said tool member defining an external non-deformable surface of a selected configuration, said external surface including at least a conical portion symmetrical around said axis of said tool member and converging toward said second end portion and an axial extension extending from said conical portion, said axial extension having a plurality of flat surfaces oriented substantially parallel with said axis of said tool member, said second end portion provided with a threaded receptor aligned on said axis of said tool member;

an elongated handle member for grasp by a hand of said user, said handle member having a longitudinal axis, a first end portion and a second end portion, said handle member provided with a passageway extending along said longitudinal axis from said first end portion to said second end portion, said first end portion being provided with a receptor communicating with said passageway, said receptor defining an interior non-deformable surface configured to be complementary to said external surface of said second end portion of said tool member so as to releasably receive said second end portion of said tool member with said axis of said tool member and said axis of said handle member being coextensive; and a transfixing rod for being received through said passageway in said handle member, said transfixing rod having a threaded first end for being threadably received in said threaded receptor of said tool member, and a second end extending from said second end portion of said handle member, said second end of said transfixing rod provided with a knurled knob proximate said second end of said handle member for readily permitting said user to rotate said transfixing rod in a first direction to advance said threaded end into said threaded receptor of said tool member to produce intimate frictional contact between said external surface of said second end portion of said receptor of said handle member so as to prevent relative transverse, axial and rotational movement between said tool member and said handle member during application of transverse, axial and rotational forces applied to said handle member, and for rotating said transfixing rod in a second direction to disengage said tool member from said handle member.

14. The surgical instrument of claim 13 wherein said axial extension of said external surface of said tool member defines a hexagonal cross-section transverse to said axis of said tool member, and wherein said external surface of said second end portion of said tool member and said internal surface of said receptor at said first end of said handle member are formed from the same material.

15. A manual surgical instrument for performing a selected surgical operation by a user, which comprises:
a tool member having a longitudinal axis, a first end portion configured to perform said selected surgical operation, and a second end portion, said second end portion of said tool member defining an external non-deformable surface including a conical portion symmetrical around said axis of said tool member and converging toward said second end portion and an axial extension to said conical portion, said axial extension provided with at least one flat surface substantially parallel to said axis, said second end portion provided with a threaded receptor aligned on said axis of said tool member;

an elongated handle member for grasp by a hand of said user, said handle member having a longitudinal axis, a first end portion and a second end portion, said handle member provided with a passageway extending along said longitudinal axis from said first end portion to said second end portion, said first end portion being provided with a receptor communicating with said passageway, said receptor defining an interior non-deformable surface including a conical portion and an extension thereto configured to be complementary to said external surface of said second end portion of said tool member so as to closely and releasably receive said second end portion of said tool member with said axis of said tool member and said axis of said handle member are prevented from relative rotation and whereby said tool member and said handle are provided with a selective rotational orientation; and a transfixing rod for being received through said passageway in said handle member, said transfixing rod having a threaded first end for being threadably received in said threaded receptor of said tool member, and a second end extending from said second end portion of said handle member, said second end portion of said transfixing rod provided with means proximate said second end of said handle member for permitting said user to readily rotate said transfixing rod in a first direction to advance said threaded end into said threaded receptor of said tool member to produce intimate contact between said external surface of said second end portion of said tool member and said internal surface of said receptor of said handle member, and for rotating said transfixing rod in a second direction to disengage said tool member from said handle member.

16. The surgical instrument of claim 15 wherein said axial extension defines a hexagonal cross-section transverse to said axis of said tool member.

17. The surgical instrument of claim 15 wherein said axial extension defines a triangular cross-section transverse to said axis of said tool member.

18. The surgical instrument of claim 15 wherein said axial extension is defines a rectangular cross-section transverse to said axis of said tool member.

* * * * *